(12) United States Patent
Alfonso Rodriguez et al.

(10) Patent No.: US 11,905,236 B2
(45) Date of Patent: Feb. 20, 2024

(54) DYNAMIC COMBINATORIAL LIBRARY BASED ON PSEUDOPEPTIDES AND ITS USE FOR THE DETECTION OF CYSTEINE AND OTHER BIOTHIOLS

(71) Applicant: CONSEJO SUPERIOR DE INVESTIGACIONES CIENTIFICAS (CSIC), Madrid (ES)

(72) Inventors: Igancio Alfonso Rodriguez, Barcelona (ES); Jordi Sola Oller, Barcelona (ES); Maria Lafuente Fabra, Barcelona (ES)

(73) Assignee: CONSEJO SUPERIOR DE INVESTIGACIONES CIENTIFICAS (CSIC), Madrid (ES)

( * ) Notice: Subject to any disclaimer, the term of this patent is extended or adjusted under 35 U.S.C. 154(b) by 806 days.

(21) Appl. No.: 17/042,667

(22) PCT Filed: Apr. 4, 2019

(86) PCT No.: PCT/ES2019/070226
§ 371 (c)(1),
(2) Date: Sep. 28, 2020

(87) PCT Pub. No.: WO2019/193231
PCT Pub. Date: Oct. 10, 2019

(65) Prior Publication Data
US 2021/0139419 A1 May 13, 2021

(30) Foreign Application Priority Data
Apr. 4, 2018 (ES) ................ ES201830330

(51) Int. Cl.
*G01N 33/58* (2006.01)
*G01N 33/68* (2006.01)
*C07C 321/06* (2006.01)

(52) U.S. Cl.
CPC ......... *C07C 321/06* (2013.01); *G01N 33/582* (2013.01); *G01N 33/6815* (2013.01)

(58) Field of Classification Search
CPC . G01N 33/582; G01N 33/6815; C07C 321/06
(Continued)

(56) References Cited

U.S. PATENT DOCUMENTS

2008/0261315 A1* 10/2008 Strongin ............ G01N 33/6815
436/106
2014/0206095 A1 7/2014 Strongin et al.
(Continued)

FOREIGN PATENT DOCUMENTS

WO 2015097041 A1 2/2015

OTHER PUBLICATIONS

Herrmann, A., Chemical Society Reviews 2014, 43, 1899--1933. (Year: 2014).*
(Continued)

*Primary Examiner* — Arlen Soderquist
(74) *Attorney, Agent, or Firm* — Hayes Soloway PC

(57) ABSTRACT

The present invention relates to a dynamic chemical network that mimics the transfer of information and ultimately produces a chemical response, for example a readable signal. More specifically, the invention discloses a dynamic system able to selectively sense a biologically-relevant analyte, such as cysteine, in its reduced or its oxidized form (cystine) in aqueous media and in a biofluid (such as urine) for diagnostic application. Due to this property, said dynamic system is useful for the detection of cysteine or its derivatives in biological fluids such as urine.

16 Claims, 6 Drawing Sheets

(58) Field of Classification Search
USPC .................................................. 436/86, 172
See application file for complete search history.

(56) References Cited

U.S. PATENT DOCUMENTS

| | | | | |
|---|---|---|---|---|
| 2016/0083344 | A1* | 3/2016 | Yoon | C07D 401/14 |
| | | | | 544/361 |
| 2017/0240568 | A1* | 8/2017 | Das | C07F 1/005 |
| 2018/0354975 | A1* | 12/2018 | Das | C07F 5/022 |
| 2020/0150128 | A1* | 5/2020 | Wolf | C07D 277/66 |

OTHER PUBLICATIONS

Maria Lafuente, "A Dynamic Chemical Network for Cystinuria Diagnosis", Journal, 2018, 8421-8424, No. 57, Angewandte Chemie International Edition.

Maria Lafuente, "Adaptive Correction from Virtually Complex Dynamic Libraries: The Role of Noncovalent Interactions in Structural Selection and Folding", Journal, 2015, 17002-17009, Chemistry—A European Journal.

Jordi Sola, "Constitutional Self-Selection from Dynamic Combinatorial Libraries in Aqueous Solution Through Supramolecular Interactions", Journal, 2014, 4564-4566, vol. 50, Chemical Communications.

Artur R. Stefankiewicz, "Diverse Topologies in Dynamic Combinatorial Libraries from Tri-and-Mono-thiols in Water: Sensitivity to Weak Supramolecular Interactions", Journal, 2013, 5820-5822, vol. 49, Chemical Communications.

Mary Sajini Devadas, "Directional Electron Transfer in Chromophore-Labeled Quantum-Sized AU25 Clusters: AU25 as an Electron Donor", Journal, 2010, 1497-1503, vol. 1, The Journal of Physical Chemistry Letters.

Dan Zhang, "A Simple Excited-State Intramolecular Proton Transfer Probe Based on a New Strategy of Thiol-Azide Reaction for the Selective Sensing of Cysteine and Glutathione", 2016, 749-752, vol. 52, Chemical Communications.

Kevin R. West, "Dynamic Combinatorial Libraries of Disulfide Cages in Water", Journal, 2005, 2615-2618, vol. 7, No. 13, Organic Letters.

* cited by examiner

DYNAMIC COMBINATORIAL LIBRARY BASED ON PSEUDOPEPTIDES AND ITS USE FOR THE DETECTION OF CYSTEINE AND OTHER BIOTHIOLS

CROSS-REFERENCE TO RELATED APPLICATIONS AND PRIORITY

This patent application claims priority from PCT Patent Application No. PCT/ES2019/070226 filed Apr. 4, 2019, which claims priority from Spanish Patent Application No. ES P20180330 filed Apr. 4, 2018. Each of these patent applications are herein incorporated by reference in its/their entirety.

The invention relates to a mixture of molecules containing thiol groups which form a dynamic chemical network based on pseudopeptidic building blocks upon disulfide exchange.

STATE OF ART

Dynamic combinatorial chemistry proposes the creation of a mixture of compounds (Dynamic Combinatorial Libraries, DCL) inter-connected through reversible chemical processes. The changes of distribution of the species involved in a DCL contain valuable information about changes in stability, with the corresponding implications in the recently emerged field of Systems Chemistry.

Small molecules containing thiols such as cysteine (Cys) play an essential role in cell function. Therefore, the selective detection of these thiols is of great importance for clinical diagnosis. However, specific and selective methods for the detection of cysteine are still scarce (D. Zhang, Z. Yang, H. Li, Z. Pei, S. Sun, Y. Xu. *Chem. Commun.*, 2016, 52, 749-752).

Solá et al. (*Chem. Commun.*, 2014, 50, 4564-4566) described the formation of a specific constitution arising from the combination of building blocks with different topologies (mono-, di- and trithiols) through disulphide chemistry in a DCL.

The document WO2015/097041 discloses a combinatorial library of molecules based on dynamic peptides able to carry out a reversible chemical reaction under physiological conditions. This DCL is useful for the discovery of therapeutically active ingredients.

DESCRIPTION OF THE INVENTION

The present invention discloses a dynamic chemical network that mimics the transfer of information and ultimately produces a chemical response, for example a readable signal. More specifically, the invention discloses a dynamic system able to selectively sense a biologically-relevant analyte, such as cysteine, in its reduced or its oxidized forms (cystine) in aqueous media and in a biofluid (such as urine) for diagnostic application.

Thus, a first aspect of the present invention relates to a mixture of molecules comprising at least a compound as defined by formula (I):

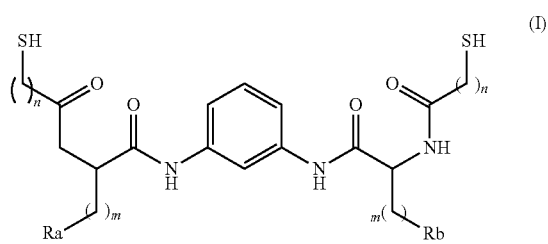

(I)

or an isomer or a salt thereof, wherein:
Ra and Rb are independently selected from H, —CONRR', —COOR, —NRR', —OH, —C(NH)NH$_2$, —CH(OH)CH$_3$, aryl-(C$_6$-C$_{10}$) or heteroaryl-(C$_6$-C$_{10}$);
R and R' are independently selected from H or alkyl-(C$_1$-C$_5$);
m is an integer selected from 0, 1, 2, 3 or 4;
n is an integer selected from 1 or 2;
and at least a compound of formula (II):

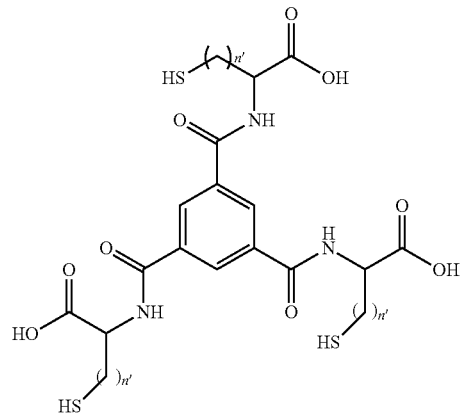

(II)

or an isomer or a salt thereof, wherein:
n' is an integer selected from 1 or 2;
and at least a compound of formula (III):

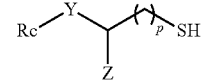

(III)

or an isomer or a salt thereof, wherein:
Rc represents an aromatic chromphore;
Y is selected from NHCO or CONH;
Z is selected from H, —NH$_2$, —OH or —COOH;
p is an integer selected from 0, 1, 2 or 3.
Preferably, the mixture of molecules as described above also comprises at least a compound of formula (IV):

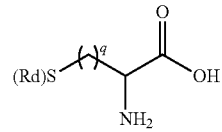

(IV)

or an isomer or a salt thereof, wherein:
Rd is selected from H or —S(CH$_2$)qCH(NH$_2$)COOH;
q is an integer selected from 1, 2 or 3.
Preferably, in the mixture of molecules as described above, m is 1 and n is 1.
Preferably, in the mixture of molecules as described above, Ra is —CONH$_2$.
Preferably, in the mixture of molecules as described above, Rb is —CONH$_2$.
Preferably, in the mixture of molecules as described above, n' is 1.

Preferably, in the mixture of molecules as described above, m is 1, n is 1 and Ra and Rb are selected from —OH, —COOH, —CONH$_2$, NH$_2$, 3-indolyl or 4-phenyl.

Preferably, in the mixture of molecules as described above, m is 2, n is 1 and Ra and Rb are selected from —COOH or —CONH$_2$.

Preferably, in the mixture of molecules as described above, m is 3, n is 1 and Ra and Rb are selected from —NHC(NH)NH$_2$ or NH$_2$.

Preferably, in the mixture of molecules as described above, m is 4, n is 1 and Ra and Rb are NH$_2$.

Preferably, in the mixture of molecules as described above, m is 0, n is 1 and Ra and Rb are —CH(OH)CH$_3$.

Preferably, in the mixture of molecules as described above, Rc is selected from the following chromophores:

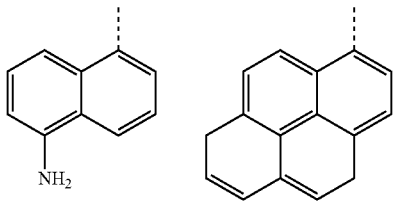

Preferably, in the mixture of molecules as described above, Y is NHCO.

Preferably, in the mixture of molecules as described above, Z is —NH$_2$.

Preferably, in the mixture of molecules as described above, p is 1.

Preferably, in the mixture of molecules as described above, Rd is H.

Preferably, in the mixture of molecules as described above, q is 1.

In the present invention, the term "aryl" refers to monocyclic or bicyclic aromatic hydrocarbon groups containing 6 to 10 carbons in the ring portion, such as phenyl, naphthyl (including 1-naphthyl and 2-naphthyl), biphenyl or indenyl. The aryl radicals may be optionally substituted by one or more substituents, such as alkyl, hydroxyl, amines, amide, cyano, halogen (F, Cl, Br and I), etc.

In the present invention, the term "heteroaryl" refers to a monocyclic or bicyclic aromatic hydrocarbon group of 5 to 10 members that consists in carbon atoms and from one to three heteroatoms selected from the group consisting in N, O and S, such as bencimidalozyl, benzothiazolyl, indolyl, piridyl, pirimidyl, pirrolyl, pirazolyl, imidazolyl, furanyl or, thiophenyl. The heteroaryl radicals may be optionally substituted by one or more substituents, such as alkyl, hydroxyl, amines, amide, cyano, halogen (F, Cl, Br and I), etc.

The term "alkyl" refers, in the present invention, to linear or branched saturated hydrocarbon chains having preferably 1 to 5 carbon atoms, and which bind to the rest of the molecule by a single bond, for example, methyl, ethyl, n-propyl, i-propyl, n-butyl, terc-butyl, sec-butyl, n-pentyl, etc. The alkyl groups may be optionally substituted by one or more substituents such as halogen, hydroxyl, alkoxyl, carboxyl, carbonyl, cyano, acyl, alkoxycarbonyl, amino, nitro, mercapto and alkylthio.

The term "chromophore" refers, in the present invention, to a chemical group capable of absorbing or emitting light selectively. Examples of chomophores can be radicals of a series of alternating single and double bonds, aromatic systems, etc. Preferably, in the present invention, chromophores contain polyaromatic systems, formed by two to five aromatic hydrocarbon rings containing 9 to 22 carbon atoms, and which bind to the rest of the molecule by a single bond, for example, naphthyl, anthracenyl, phenanthrenyl, pyrenyl, benzopyrenyl. The polyaromatic systems radicals may be optionally substituted by one or more substituents, such as alkyl, hydroxyl, amines, amide, cyano, halogen (F, Cl, Br and I), aryl, etc.

The compounds of the present invention represented by formula I, II III and IV may be comprised of isomers, including optical isomers or enantiomers, depending on the presence of chiral centres. Isomers, enantiomers or diastereomers and mixtures thereof fall within the scope of this invention. Enantiomers or diastereomers, and their mixtures, can be separated by conventional techniques.

Another aspect of the invention relates to a dynamic combinatorial library (DCL) comprising the mixture of molecules as previously described.

The terms "dynamic combinatorial library or DCL" are defined herein to mean a combinatorial library or a mixture which is dynamic in the sense that molecules of the combinatorial library or mixture may reorganize between each other by exchanging specific atomic groups or forming dynamic covalent bonds. Notably such reorganization may occur when one or more external conditions change, for example such as changing one or more chemical parameters, such as for example adding one or more potentially active molecules to the library or mixture, and/or adding chemical additives to the library or mixture, or adding or changing solvent of the library or mixture, and/or one or more physical parameters, such as for example temperature, pressure, pH, electric current, magnetic or electromagnetic radiation, etc.

For the preparation of DCLs, building blocks (BBs) I, II and III are mixed at pH close to neutrality in aqueous media or any other suitable solvent, such as H$_2$O-DMSO. A dynamic library of a mixture of different covalent compounds upon disulfide exchange is formed, that is homo and/or heterodimers, trimers, or tetramers (DCL1). Once compound IV is added to the media, the dynamic library is rearranged to obtain mainly most stable compound V, formed by I, II and IV, releasing the fluorophore which is a dimer of III in its oxidized form [III]$_2$ (Scheme 1).

Scheme 1

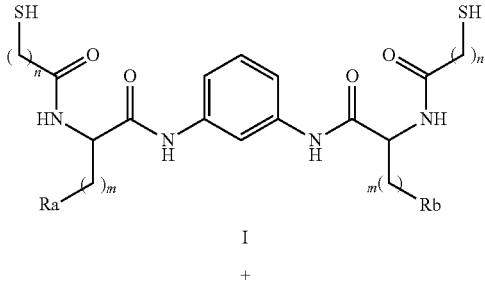

I

+

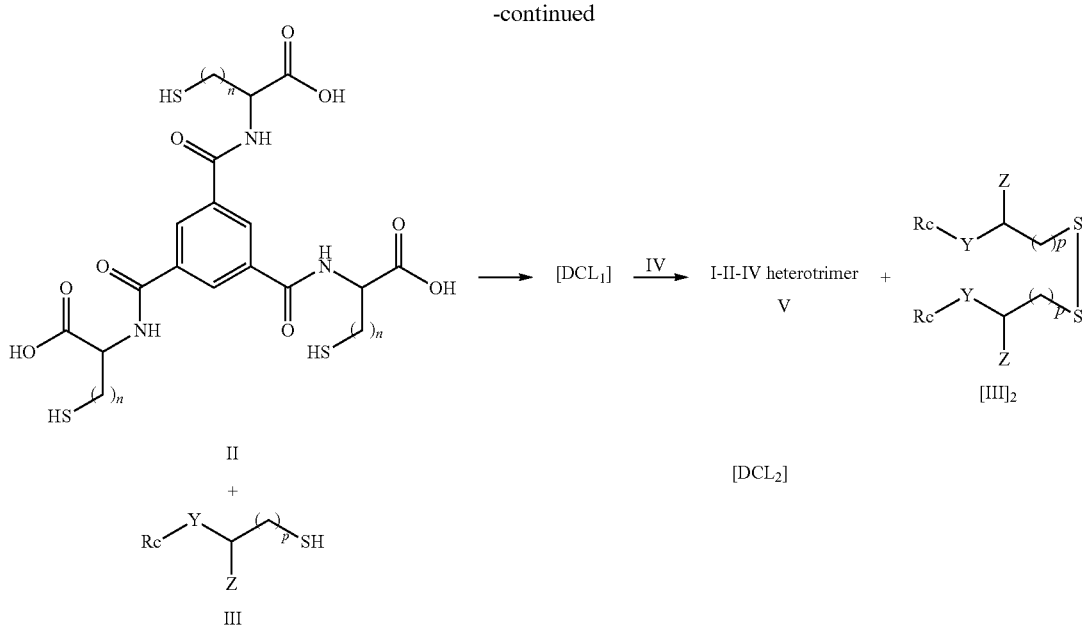

Thus, the invention relates to a DCL formed by a mixture of compounds type I, II and III upon disulfide exchange, forming different dynamic dimers, trimers and tetramers. Accordingly the invention relates to molecules comprising intramolecular disulfide bonds. The invention also relates to a DCL2 formed by adding the compound IV to said mixture of compounds, thus forming a dynamic library of I, II, III, and IV.

The invention also relates to the dynamic exchange between III and IV of the above DCL forming a defined heterotrimer formed by I, II and IV and an excited homodimer or excimer $[III]_2$.

Preferably, the heterotrimer formed in the DCL2 is that comprising Ia, IIa and IVa-e and excimer is $[IIIa\text{-e}]_2$. More preferably, the heterotrimer is Va, comprising Ia, IIa and IVa and excimer is $[IIIa]_2$. (Scheme 2)

Scheme 2.
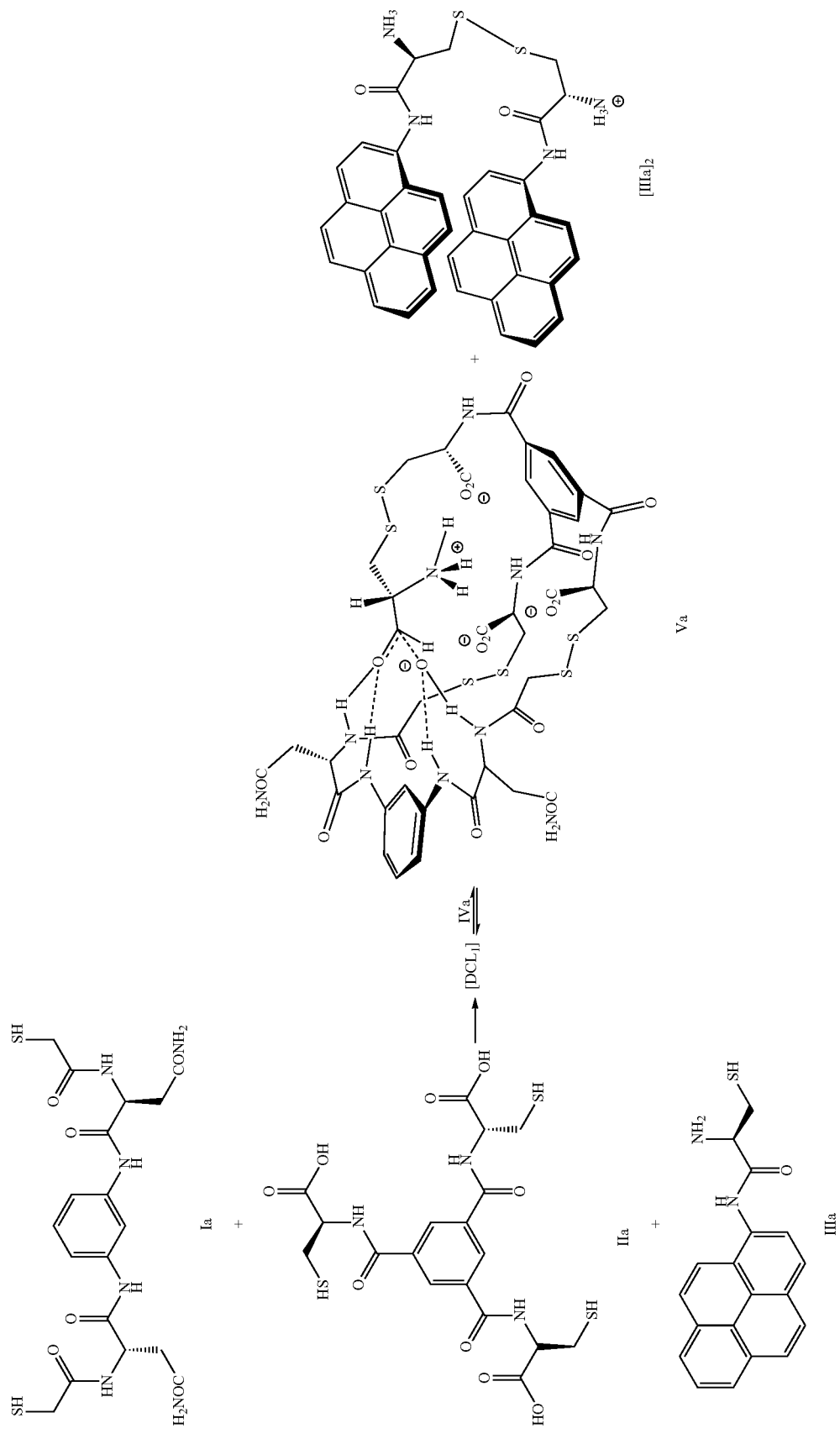

Another aspect of the invention relates to an in vitro method for the detection of a compound of formula (IV) as described above, in a sample, comprising the following steps:
a) mixing at least a compound of formula (I) with at least a compound of formula (II) and at least a compound of formula (III) as described above;
b) contacting the sample comprising the compound of formula (IV) with the mixture of step (a);
c) measuring the fluorescence emission of the mixture obtained in step (b);
d) detecting a significant deviation from a standard and
e) assigning the sample to the group of samples comprising a compound of formula (IV) when a significant difference has been detected in stage (d).

Preferably, the fluorescence emission measured in step (c) is due to the formation of excimer [III]$_2$, which can be read by spectroscopy, preferably fluorescence spectroscopy.

Thus, presence of compound IV in the library can be determined by analysing the ratio between the emission band due to the monomer III, in a range between 350 and 425 nm, and the emission band of the excimer, in a range between 450 and 550 nm. More preferably, the ratio is between $I_{\lambda 501}/I_{\lambda 385}$.

Preferably, in the method, the molecule of formula (IV) is cysteine (IVa or Cys) or its oxidized form cystine (IVb or CySS).

Preferably, in the method, the molecule of formula (IV) is in a biological sample. More preferably the biological sample is urine.

Another aspect of the invention refers to the use of the DCLs of the invention for the diagnosis of diseases related to the presence of cysteine or cystine in a biological fluid. Preferably, the disease is cystinuria or cystinosis. More preferably the disease is cystinuria.

Another aspect of the invention refers to a kit for the detection of a compound of formula IV in a sample, in particular cysteine or cystine, comprising a mixture of compounds of formula I, II and III as described above. Also, the kit may include other components and reagents necessary to carry out sample analysis.

Unless otherwise defined, all technical and scientific terms used herein have the same meaning as commonly understood by one of ordinary skilled in the art to which this invention belongs. Methods and materials similar or equivalent to those described herein can be used in the practice of the present invention. Throughout the description and claims the word "comprise" and its variations are not intended to exclude other technical features, additives, components, or steps. Additional objects, advantages and features of the invention will become apparent to those skilled in the art upon examination of the description or may be learned by practice of the invention. The following examples and drawings are provided by way of illustration and are not intended to be limiting of the present invention.

Compounds of formula I, II, III can be prepared following different methods known by any person skilled in the field of organic synthesis, particularly following the general processes shown in the following schemes. The starting materials for the preparative methods are commercially available or they can be prepared by means of methods of the literature.

Compounds of Formula I:
According to scheme 3, a carboxylic acid 1, wherein PG represents a protecting groups, such as Fmoc for the amine, is reacted with the 1,3-diaminebenzene to obtain the diamide (i), using a coupling agent such as, for example the combination of N,N'-dicyclohexylcarbodiimide (DCC) and 1-hydroxybenzotriazole (HOBt) in an appropriate solvent such as N,N-dimethylformamide. After deprotection of the compound (i) obtained under the appropriate basic conditions, such as piperidine, the deprotected compound (ii) is acylated with a protected-sulfanyl acid. The reaction can be carried out in the presence of a suitable coupling agent, for example 1-ethyl-3-(3-dimethylaminopropyl)carbodiimide (EDC) and HOBt. Finally the resulting compound (iii) is deprotected to obtain the corresponding free thiol (I).

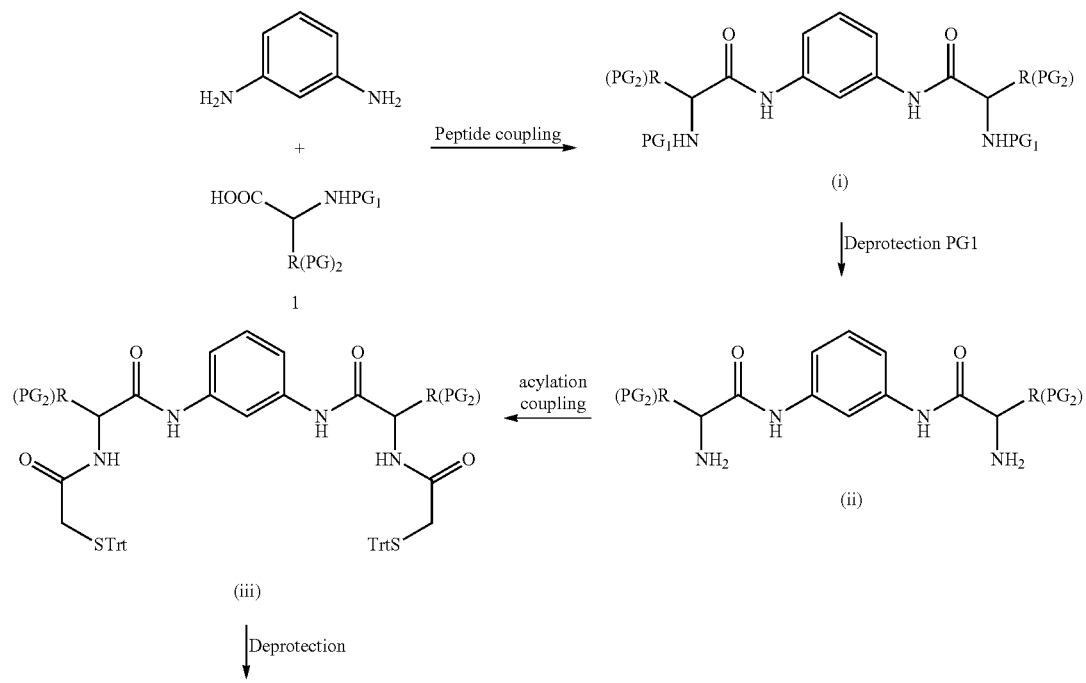

Scheme 3

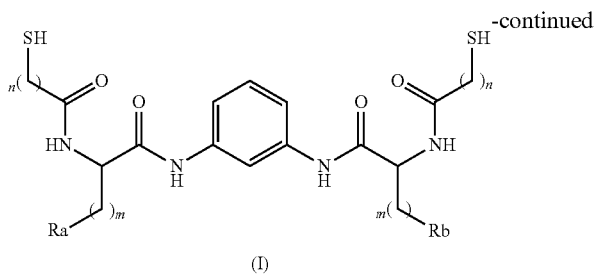

(I)

Compounds of Formula (II):

According to scheme 4, II can be synthesised as previously described in K. R. West, K. D. Bake and S. Otto, *Org. Lett.*, 2005, 7, 2615-2618.

Scheme 4

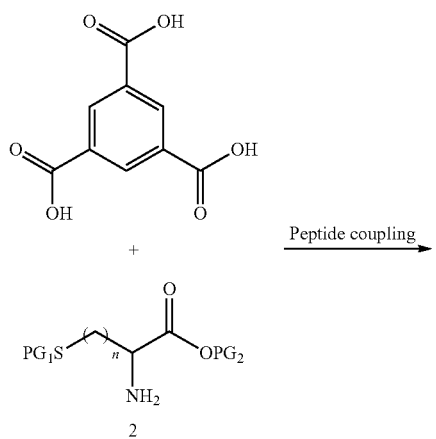

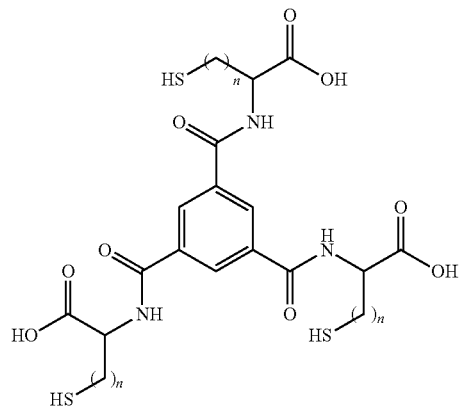

II

Compounds of Formula (III):

According to scheme 5, a polyaromatic acid (v) or amine (vii) is coupled with the corresponding protected-sufanyl amine (vi) or acid (viii), respectively using a suitable coupling agent, such as EDC and HOBt in basic conditions. The resulting compound 3 can be deprotected in acidic conditions, such as for example trifluoracetic acid.

Scheme 5

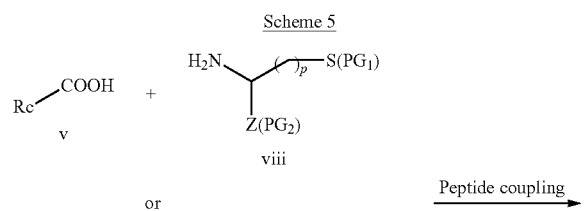

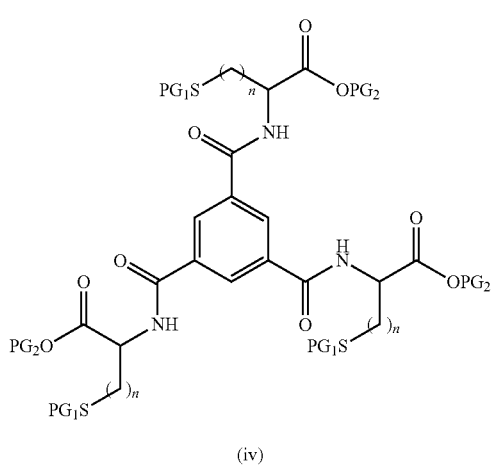

(iv)

↓ Deprotection

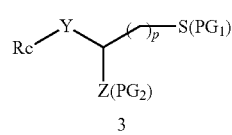

↓ deprotection

-continued

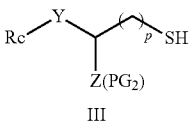

III

EXAMPLES

Figure 1:
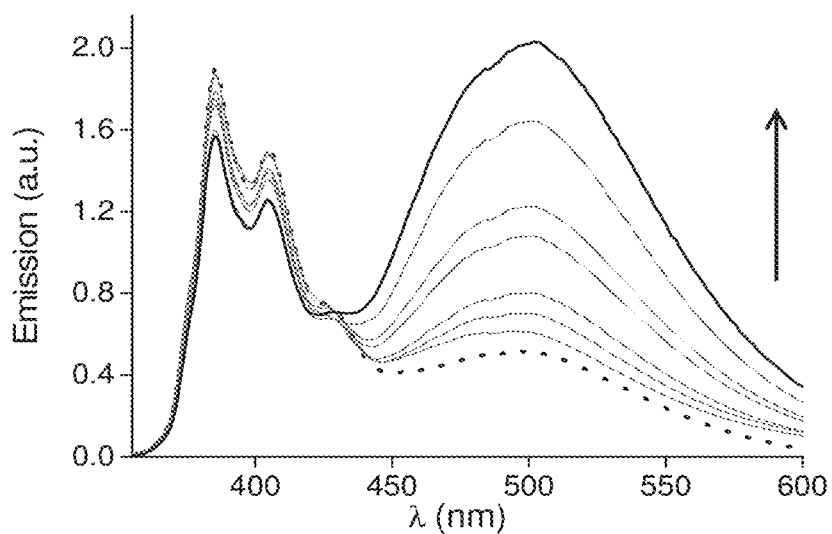
FIG. 1: Shows the fluorescence emission spectra of the dynamic library formed by Ia, IIa and IIIa (sensor) (25% DMSO in aqueous bis-tris buffer at pH 6.5) and under increasing concentrations of Cys. [Cys]=No L-Cys (dotted line), 0.025 mM, 0.05 mM, 0.1 mM, 0.25 mM, 0.5 mM, 1 mM, 2.5 mM.

1. Synthesis of the Compounds of the Mixture of Molecules of the Invention

A) Compounds of formula (I)

Step 1: To a solution of protected amino acid 1 (PG1 is Fmoc and PG2 is Boc or tBu) (7.11 mmol) in dry DMF (15 mL), HOBt (1.25 g, 9.27 mmol) and DCC (2.23 g, 10.8 mmol) were added under nitrogen atmosphere. The resulting mixture was cooled down to 0° C. and then a solution of m-phenylenediamine (334 mg, 3.09 mmol) in dry DMF (10 mL) was added via cannula. The mixture was stirred at room temperature for 60 hours, filtered, and the filtrate was diluted with DCM, washed with saturated aqueous NaHCO3 and saturated aqueous NaCl, dried over MgSO4 and concentrated under reduced pressure. The residue was purified by flash chromatography using AcOEt/hexane as eluents to yield compounds (i).

Step 2: Compounds (i) (0.5 mmol) were dissolved in 4.0 mL of 20% piperidine in dry DMF. The mixture was allowed to react for 4 hours and then diethyl ether was added over the reaction mixture and the product was filtered off and washed with diethyl ether to obtain compounds (ii) which were used without further purification.

Step 3: Tritylsulfanyl acetic acid (501 mg, 1.50 mmol) was dissolved in dry DMF (20 mL) and EDC·HCl (312 mg, 1.63 mmol), HOBt (228 mg, 1.69 mmol) and DIPEA (1.6 mL, 4.59 mmol) were added over the solution. The reaction mixture was cooled down to 0° C. and (ii) (0.715 mmol) was added over the mixture. The mixture was stirred at room temperature for 48 hours and then diluted with DCM, washed with saturated aqueous NaHCO3 and saturated aqueous NaCl, and dried under reduced pressure. The crude product was purified by flash chromatography using AcOEt/ hexane as eluents to give compounds (iii).

Step 4: To a solution of (iii) (0.16 mmol) in DCM (1.0 mL), TFA (8.5 mL), TIS (332 μL, 1.28 mmol) and EDT (160 μL, 1.91 mmol) were added rapidly and under stirring. The reaction mixture was stirred at room temperature for 2 hours, after which the solvents were partially evaporated using a $N_2$ flow. Diethyl ether was added over the reaction mixture and the product was filtered off and washed with diethyl ether. The product was purified by reversed-phase flash chromatography using a mixture of MeCN+0.07% (v/v) TFA and H2O+0.1% (v/v) TFA as mobile phase. Compounds (I) were obtained after lyophilisation of the mobile phase.

(2S,2'S)—N1,N1'-(1,3-phenylene)bis(2-(2-mercaptoacetamido)succinamide) (Ia) (Asn): 1H NMR (400 MHz, DMSO-d6): δ=9.97 (s, 2H), 8.34 (d, 2H), 7.93 (t, 1H), 7.36 (s, 2H), 7.29 (dd, 2H), 7.24-7.15 (m, 1H), 6.91 (s, 2H), 4.67 (q, 2H), 3.17 (d, 4H), 2.73 (t, 2H), 2.62-2.41 (m, 4H) ppm. HRMS (ESI+) calcd. for $C_{18}H_{24}N_6O_6S_2$ [M+H]+ (m/z): 485.1277, found: 485.1279.

(2S,2'S)—N1,N1'-(1,3-phenylene)bis(2-(2-mercaptoacetamido)pentanediamide) (Ib) (Gln): 1H NMR (400 MHz, DMSO-d6): δ=10.09 (s, 2H), 8.30 (d, J=7.7 Hz, 2H), 7.96 (t, 1H), 7.35-7.27 (m, 4H), 7.26-7.20 (m, 1H), 6.77 (s, 2H), 4.39 (td, 2H), 3.25-3.12 (m, 4H), 2.75 (t, 2H), 2.22-2.04 (m, 4H), 1.99-1.88 (m, 2H), 1.88-1.76 (m, 2H) ppm. HRMS (ESI+) calcd. for $C_{20}H_{28}N_6O_6S_2$ [M+H]+ (m/z): 513.1590, found: 513.1592.

(2S,2'S)—N,N'-(1,3-phenylene)bis(3-hydroxy-2-(2-mercaptoacetamido)propanamide) (Ic) Ser: 1H NMR (400 MHz, MeOD-d4): δ=7.92 (t, 1H), 7.37-7.30 (m, 2H), 7.29-7.23 (m, 1H), 4.56 (t, 2H), 3.93-3.82 (m, 4H), 3.28 (s, 4H) ppm. HRMS (ESI+) calcd. for $C_{16}H_{22}N_4O_6S_2$ [M+H]+ (m/z): 431.1059, found: 431.1054.

(2S,2'S)—N,N'-(1,3-phenylene)bis(3-hydroxy-2-(2-mercaptoacetamido)butanamide) (Id) (Thr): 1H NMR (400 MHz, MeOD-d4): δ=9.80 (s, 2H), 8.18 (d, 2H), 7.95-7.89 (m, 1H), 7.36-7.30 (m, 2H), 7.29-7.23 (m, 1H), 4.48-4.42 (m, 2H), 4.24 (qd, 2H), 3.35-3.29 (m, 4H), 1.24 (d, 6H) ppm. HRMS (ESI+) calcd. for $C_{18}H_{26}N_4O_6S_2$ [M+H]+ m/z): 459.1372, found: 459.1371.

(2S,2'S)—N,N'-(1,3-phenylene)bis(3-(4-hydroxyphenyl)-2-(2-mercaptoacetamido)propanamide) (Ie) (Tyr): 1H NMR (400 MHz, DMSO-d6): δ=10.11 (s, 2H), 9.17 (br s, 2H), 8.34 (d, 2H), 7.88 (t, 1H), 7.32-7.25 (m, 2H), 7.25-7.18 (m, 1H), 7.06 (d, 4H), 6.64 (d, 4H), 4.58 (td, 2H), 3.12 (d, 4H), 2.92 (dd, 2H), 2.75 (dd, 2H), 2.63 (t, 2H) ppm. HRMS (ESI+) calcd. for $C_{28}H_{30}N_4O_6S_2$ [M+H]+(m/z): 583.1685. found: 583.1696.

(2S,2'S)—N,N'-(1,3-phenylene)bis(3-(1H-indol-3-yl)-2-(2-mercaptoacetamido)propanamide) (If) (Trp): 1H NMR (400 MHz, DMSO-d6): δ=10.82 (d, 2H), 10.17 (s, 2H), 8.37 (d, 2H), 7.93 (s, 1H), 7.64 (d, 2H), 7.35-7.27 (m, 4H), 7.24-7.18 (m, 1H), 7.16 (d, 2H), 7.05 (ddd, 2H), 6.97 (ddd, 2H), 4.72 (td, 2H), 3.23-3.11 (m, 6H), 3.02 (dd, 2H), 2.65 (t, 2H) ppm. HRMS (ESI+) calcd. for $C_{32}H_{32}N_6O_4S_2$ [M+H]+ (m/z): 629.2004, found: 629.2003.

(3S,3'S)-4,4'-(1,3-phenylenebis(azanediyl))bis(3-(2-mer-captoacetamido)-4-oxobutanoic acid) (Ig) (Asp): 1H NMR (400 MHz, MeOD-d4): δ=7.85 (t, 1H), 7.35-7.29 (m, 2H), 7.28-7.22 (m, 1H), 4.90-4.81 (m, 2H), 3.24 (s, 4H), 2.91 (dd, 2H), 2.78 (dd, 2H) ppm. HRMS (ESI+) calcd. for C18H22N4O8S2 [M+H]+ (m/z): 487.0957, found: 487.0956.

(4S,4'S)-5,5'-(1,3-phenylenebis(azanediyl))bis(4-(2-mer-captoacetamido)-5-oxopentanoic acid) (Ih) Glu: 1H NMR (400 MHz, MeOD-d4): δ=7.90 (t, 1H), 7.35-7.30 (m, 2H), 7.29-7.23 (m, 1H), 4.53 (dd, 2H), 3.24 (s, 4H), 2.45 (t, 4H), 2.25-2.12 (m, 2H), 2.08-1.96 (m, 2H) ppm. HRMS (ESI+) calcd. for $C_{20}H_{26}N_4O_8S_2$ [m+H]+ (m/z): 515.1270, found: 515.1271.

(2S,2'S)—N,N'-(1,3-phenylene)bis(6-amino-2-(2-mer-captoacetamido)hexanamide) (Ii) (Lys): 1H NMR (400 MHz, MeOD-d4): δ=8.01-7.96 (m, 1H), 7.35-7.19 (m, 3H), 4.49 (dd, 2H), 3.24 (s, 4H), 2.93 (t, 4H), 2.01-1.87 (m, 2H), 1.86-1.63 (m, 6H), 1.62-1.39 (m, 4H) ppm. HRMS (ESI+) calcd. for $C_{22}H_{36}N_6O_4S_2$ [M+H]+ (m/z): 513.2318, found: 513.2319.

(2S,2'S)—N,N'-(1,2-phenylene)bis(5-amino)pentana-mide) (Ij) (Orn(L 1H NMR (400 MHz, MeOD-d4): δ=8.02-7.97 (m, 1H), 7.34-7.18 (m, 3H), 4.54 (dd, 2H), 3.25 (s, 4H), 3.07-2.90 (m, 4H), 2.05-1.89 (m, 2H), 1.88-1.68 (m, 6H) ppm. HRMS (ESI+) calcd. for $C_{20}H_{32}N_6O_4S_2$ [M+H]+ (m/z): 485.2005, found: 485.2007.

(2S,2'S)—N,N'-(1,3-phenylene)bis(5-guanidino-2-(2-mercaptoacetamido)pentanamide) (Ik) Arg: 1H NMR (400 MHz, MeOD-d4): δ=7.99 (s, 1H), 7.33-7.20 (m, 3H), 4.52 (dd, 2H), 3.29-3.11 (m, 8H), 2.00-1.87 (m, 2H), 1.86-1.57 (m, 6H) ppm. HRMS (ESL+) calcd. for $C_{22}H_{36}N_{10}O_4S_2$ [M+H]+ (m/z): 569.2441, found: 569.2435.

B) Compounds of formula (II)

Compounds of formula (II) can be synthesised as previously described in K. R. West, K. D. Bake and S. Otto, *Org. Lett.*, 2005, 7, 2615-2618.

2,2',2"-(benzenetricarbonyltris(azanediyl))tris(3-mercap-topropanoic acid) (IIa) 1H-NMR (500 MHz, DMSO-d6): δ 9.04 (d, 1H), 8.52 (s, 1H), 4.58 (m, 1H) 3.03 (m, 1H), 2.93 (m, 1H), 2.61 (t, 1H) ppm. HRMS: Calc. for $C_{18}H_{21}N_3O_9S_3$ [M+H]+ 520.0518, found 520.0526.

C) Compounds of Formula (III)

Compounds of formula (III) can be synthesized as follows:

Synthesis of Compound IIIa

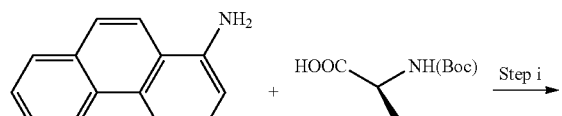

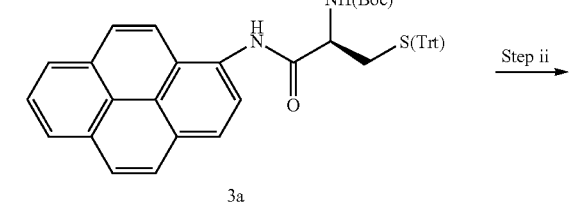

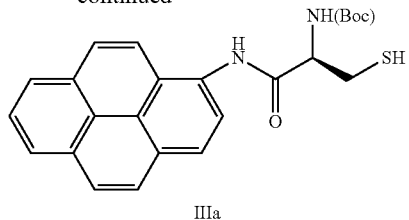

IIIa (R)-2-amino-N-(pyren-1-yl)-3-(tritylthio)propanamide (3a): Boc-Cys(Trt)-OH (2.134 g, 4.60 mmol) was dissolved in dry DMF (6 mL) and then HBTU (2.094 g, 5.52 mmol) and HOBt (0.746 g, 5.52 mmol) were added. The reaction mixture was stirred during 2 min and after 1-aminopyrene (200 mg, 0.92 mmol) was added. The solution was stirred at room temperature under an inert atmosphere of Ar for 5 hours (TLC monitoring). The mixture was diluted with DCM, washed with saturated aqueous $NaHCO_3$ and saturated aqueous NaCl, dried over MgSO4 and concentrated under reduced pressure. The crude product was purified by flash chromatography using EtOAc/hexane/toluene as eluent (from 20/60/20 to 40/40/20) to give 311 mg (51% yield) of 3a as a light pink solid.

$^1$H NMR (400 MHz, CDCl$_3$-d): δ=8.90 (s, 1H, NHCOC*H), 8.46 (d, 1H, CH$_{Ar}$), 8.19-8.11 (m, 3H, CH$_{Ar}$), 8.09-7.96 (m, 4H, CH$_{Ar}$)), 8.00 (s, 1H, CH$_{Ar}$), 7.52 (dd, 6H, CH$_{Ar}$), 7.33 (dd, 6H, CH$_{Ar}$), 7.26 (d, 3H, CH$_{Ar}$), 4.98 (d, 1H, C*HNHCO), 4.24-4.11 (m, 1H, C*H), 2.89 (ddd, 2H, C*HCH$_2$), 1.53 (s, 9H, CH$_3$) ppm. HRMS (ESI$^-$) calcd. for $C_{43}H_{38}N_2O_3S$ [M–H]$^-$ (m/z): 661.2575, found: 661.2525.

(R)-2-amino-3-mercapto-N-(pyren-1-yl)ppropanamide (IIIa): To a solution of 3a (280 mg, 0.42 mmol) in DCM (1.5 mL), 1 mL of trifluoroacetic acid (TFA), 1,2-Ethanedithiol (EDT, 0.64 mL, 7.61 mmol) and triisopropylsilane (TIS, 1.30 mL, 6.34 mmol) were added rapidly and under stirring. The reaction mixture was stirred at room temperature for 2 hours, after which the solvents were partially evaporated using a N2 flow. Diethyl ether was added over the reaction mixture and the product was filtered off and washed with diethyl ether. The product was purified by reversed-phase flash chromatography using a mixture of MeCN+0.07% (v/v) TFA and H2O+0.1% (v/v) TFA as mobile phase (gradient: from 0% to 10% MeCN in H2O). After lyophilization 75 mg (55% yield) of IIIa.1TFA were obtained as a white solid.

$^1$H NMR (400 MHz, MeOH-d$_4$): δ=8.29-8.17 (m, 6H, H$_5$, H$_6$, H$_8$, H$_{10}$, H$_{12}$, H$_{13}$), 8.11 (q, 2H, H$_2$, H$_3$), 8.05 (t, 1H, H$_9$), 4.48 (dd, 1H, C*HCH$_2$), 3.38-3.24 (dd, 2H, C*HCH$_2$) ppm. HRMS (ESI$^+$) calcd. for $C_{19}H_{16}N_2OS$ [M+H]$^+$ (m/z): 321.1061, found: 321.1041.

Synthesis of Compound IIIb

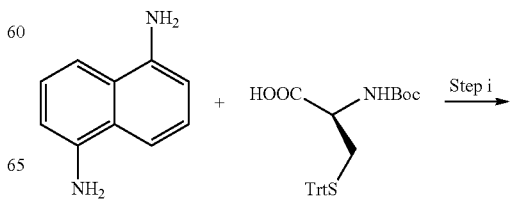

-continued

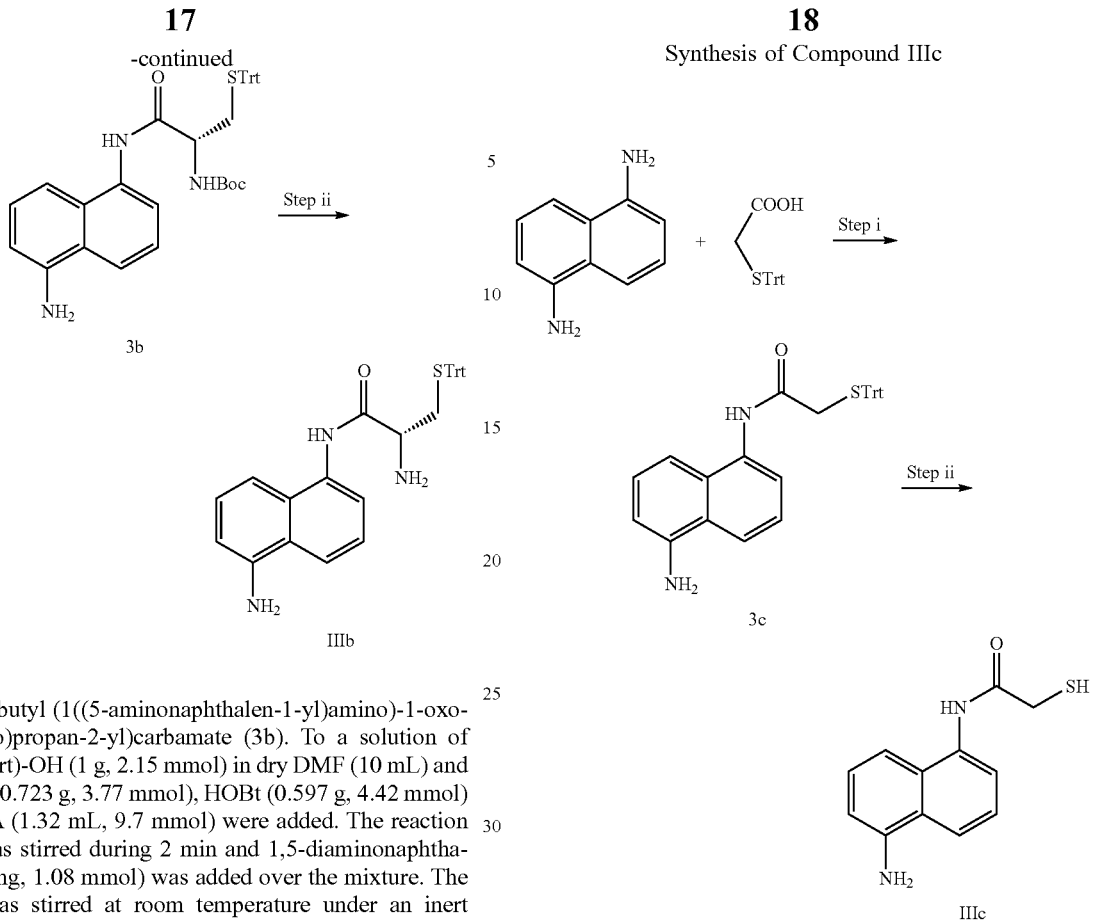

3b

IIIb

Synthesis of Compound IIIc

3c

IIIc (R)-tert-butyl (1((5-aminonaphthalen-1-yl)amino)-1-oxo-3-(tritylthio)propan-2-yl)carbamate (3b). To a solution of Boc-Cys(Trt)-OH (1 g, 2.15 mmol) in dry DMF (10 mL) and EDC·HCl (0.723 g, 3.77 mmol), HOBt (0.597 g, 4.42 mmol) and DIPEA (1.32 mL, 9.7 mmol) were added. The reaction mixture was stirred during 2 min and 1,5-diaminonaphthalene (170 mg, 1.08 mmol) was added over the mixture. The solution was stirred at room temperature under an inert atmosphere of Ar for 48 hours, and the formation of the product was followed by TLC. The mixture was diluted with DCM, washed with saturated aqueous NaHCO3 and saturated aqueous NaCl, and dried under reduced pressure. The crude product was purified by flash chromatography using EtOAc/Hexane as eluent (from 30% to 50% EtOAc) to give 356 mg (55% yield) of 3b as a dark pink solid.

$^1$H NMR (400 MHz, CDCl$_3$-d): δ=8.51 (s, 1H, CONH), 7.99 (d, 1H, CH$_{Ar}$), 7.62 (d, J=8.5 Hz, 1H, CH$_{Ar}$), 7.46 (d, 5H), 7.39 (t, 1H), 7.32-7.19 (m, 12H, CH$_{Ar}$, CONH), 6.80-6.73 (m, 2H, CH$_{Ar}$), 4.90 (d, 1H, C*HCH$_2$), 2.80 (ddd, 2H, CH$_2$STrt), 1.46 (s, CH$_3$) ppm HRMS (ESI$^+$) calcd. for C$_{37}$H$_{37}$N$_3$S [M+H]$^+$ (m/z): 604.2634, found: 604.2637.

(R)-2-amino-N-(5-aminonaphthalen-1-yl)-3-mercaptopropanamide (IIIb). To a solution of 3b (200 mg, 0.191 mmol) in DCM (1 mL), 1 mL of trifluoroacetic acid (TFA), 1,2-Ethanedithiol (EDT, 0.3 mL, 3.44 mmol) and triisopropylsilane (TIS, 0.6 mL, 2.29 mmol) were added rapidly and under stirring. The reaction mixture was stirred at room temperature for 2 hours, after which the solvents were partially evaporated using a N2 flow. Diethyl ether was added over the reaction mixture and the product was filtered off and washed with diethyl ether. The product was purified by reversed-phase flash chromatography using a mixture of MeCN+0.07% (v/v) TFA and H2O+0.1% (v/v) TFA as mobile phase (gradient: from 0% to 10% MeCN in H2O). After lyophilisation 77 mg (83% yield) of IIIb.2TFA were obtained as a white solid.

$^1$H NMR (400 MHz, MeOH-d$_4$): δ=7.92 (d, 2H, CH$_{Ar}$), 7.75 (d1H, CH$_{Ar}$), 7.61 (t, 1H, CH$_{Ar}$), 7.50 (t, 1H, CH$_{Ar}$), 7.36 (d, 1H, CH$_{Ar}$), 4.38 (t, 1H, C*HCH$_2$), 3.30-3.12 (dd, 2H, CH$_2$SH). HRMS (ESI$^+$) calcd. for C$_{13}$H$_{15}$N$_3$OS [M+H]$^+$ (m/z): 262.1014, found: 262.1001.

N-(5-aminonaphthalen-1-yl)-2-(tritylthio)acetamide (3c). Tritylsulfanyl acetic acid (500 mg, 1.50 mmol) was dissolved in dry DMF (6 mL) and EDC·HCl (383 mg, 2 mmol), HOBt (304 mg, 2.25 mmol) and DIPEA (0.87 mL, 5 mmol) were added over the solution. The reaction mixture was stirred during 2 min and 1,5-diaminonaphthalene (158 mg, 1 mmol) was added over the mixture. The solution was stirred at room temperature under an inert atmosphere of Ar for 48 hours, and the formation of the product was followed by TLC. The mixture was diluted with DCM, washed with saturated aqueous NaHCO3 and saturated aqueous NaCl, and dried under reduced pressure. The crude product was purified by flash chromatography using EtOAc/Hexane as eluent (from 30% to 50% EtOAc) to give 287 mg (61% yield) of 3c as a pink solid.

$^1$H NMR (400 MHz, CDCl3-d): δ=8.44 (s, 1H, CH2CONH), 7.83 (d, 1H, CH$_{Ar}$), 7.61 (d, 1H, CH$_{Ar}$), 7.48 (d, 6H, CH$_{Ar}$), 7.37 (t, 1H, CH$_{Ar}$), 7.30-7.23 (m, 7H, CH$_{Ar}$), 7.18 (t, 3H, CH$_{Ar}$), 7.06 (d, 1H, CH$_{Ar}$), 6.78 (d, 1H, CH$_{Ar}$), 3.46 (s, 2H, CH$_2$CONH) ppm. HRMS (ESI$^+$) calcd. for C$_{31}$H$_{26}$N$_2$OS [M+H]$^+$ (m/z): 475.1844, found: 475.1815.

N-(5-aminonaphthalen-1-yl)-2-mercaptoacetamide (IIIc). To a solution of 3c (166 mg, 0.35 mmol) in DCM (1 mL), 1 mL of trifluoroacetic acid (TFA), 1,2-Ethanedithiol (EDT, 0.53 mL, 6.30 mmol) and triisopropylsilane (TIS, 1.07 mL, 5.24 mmol) were added rapidly and under stirring. The reaction mixture was stirred at room temperature for 2 hours, after which the solvents were partially evaporated using a N2 flow. Diethyl ether was added over the reaction mixture and the product was filtered off and washed with diethyl ether. The product was purified by reversed-phase flash chromatography using a mixture of MeCN+0.07% (v/v)

TFA and H2O+0.1% (v/v) TFA as mobile phase (gradient: from 0% to 8% MeCN in H2O). After lyophilisation 60 mg (51% yield) of IIIc·1TFA were obtained as a white solid.

$^1$H NMR (400 MHz, MeOH-d$_4$): δ=7.96 (d, 1H, CH$_{Ar}$), 7.88 (d, 1H, CH$_{Ar}$), 7.74 (d, 1H, CH$_{Ar}$), 7.63 (t, 1H, CH$_{Ar}$), 7.53 (t, 1H, CH$_{Ar}$), 7.41 (d, 1H, CH$_{Ar}$), 3.48 (s, 2H, CH$_2$SH) ppm. HRMS (ESI$^+$) calcd. for C$_{12}$H$_{12}$N$_2$OS [M+H]$^+$ (m/z): 233.3035, found: 233.3015.

Synthesis of Compound IIId

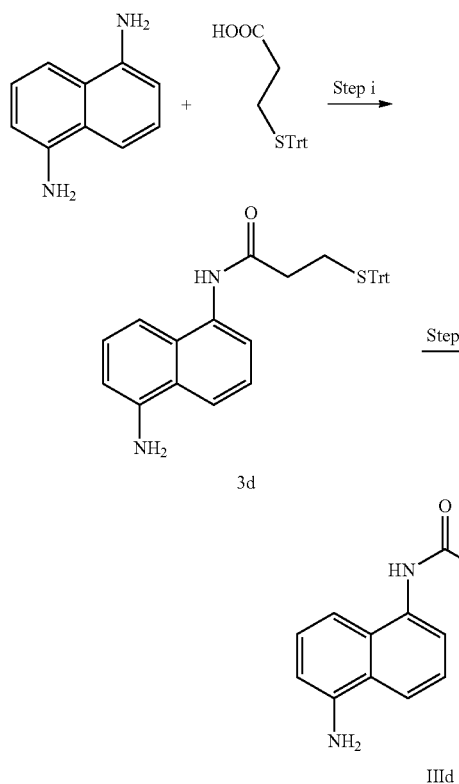

N-(5-aminonaphthalen-1-yl)-3-(tritylthio)propanamide (3d). To a solution of 3-(Tritylsulfanyl)propanoic acid (500 mg, 1.43 mmol) in dry DMF (10 mL), EDC·HCl (383 mg, 2 mmol), HOBt (304 mg, 2.25 mmol) and DIPEA (0.87 mL, 5 mmol) were added. The reaction mixture was stirred during 2 min and 1,5-diaminonaphthalene (158 mg, 1 mmol) was added over the mixture. The solution was stirred at room temperature under an inert atmosphere of Ar for 48 hours, and the formation of the product was followed by TLC. The mixture was diluted with DCM, washed with saturated aqueous NaHCO3 and saturated aqueous NaCl, and dried under reduced pressure. The crude product was purified by flash chromatography using EtOAc/Hexane as eluent (from 30% to 50% EtOAc) to give 301 mg (62% yield) of 3d as a dark pink solid.

$^1$H NMR (400 MHz, DMSO-d): δ=9.70 (s, 1H, CONH), 7.90 (d, 1H, CH$_{Ar}$), 7.54 (d, 1H, CH$_{Ar}$), 7.38-7.32 (m, 12H, CH$_{Ar}$), 7.30-7.17 (m, 6H, CH$_{Ar}$), 6.69 (dd, 1H, CH$_{Ar}$), 5.73 (s, 2H, NH$_2$), 2.56 (t, 2H, COCH$_2$CH$_2$), 2.39 (t, 2H, CH$_2$CH$_2$STrt) ppm. HRMS (ESI$^+$) calcd. for C$_{32}$H$_{28}$N2OS [M+H]$^+$ (m/z): 489.2001, found: 489.2003.

N-(5-aminonaphthalen-1-yl)-3-mercaptopropanamide (IIId). To a solution of 3d (240 mg, 0.49 mmol) in DCM (1 mL), 1 mL of trifluoroacetic acid (TFA), 1,2-Ethanedithiol (EDT, 0.74 mL, 8.84 mmol) and triisobutylsilane (TIS, 1.52 mL, 5.89 mmol) were added rapidly and under stirring. The reaction mixture was stirred at room temperature for 2 hours, after which the solvents were partially evaporated using a N2 flow. Diethyl ether was added over the reaction mixture and the product was filtered off and washed with diethyl ether. The product was purified by reversed-phase flash chromatography using a mixture of MeCN+0.07% (v/v) TFA and H2O+0.1% (v/v) TFA as mobile phase (gradient: from 0% to 10% MeCN in H2O). After lyophilisation 107 mg (61% yield) of IIId·1TFA were obtained as a white solid.

$^1$H NMR (400 MHz, MeOH-d$_4$): δ=8.01 (d, 1H, CH$_{Ar}$), 7.87 (d, 1H, CH$_{Ar}$), 7.69 (d, 1H, CH$_{Ar}$), 7.63 (t, 1H, CH$_{Ar}$), 7.52 (t, 1H, CH$_{Ar}$), 7.43 (d, 1H, CH$_{Ar}$), 3.28 (dt, 2H, COCH$_2$CH$_2$), 2.86 (d, 2H, CH$_2$CH$_2$SH) ppm. HRMS (ESI$^+$) calcd. for C$_{13}$H$_{14}$N$_2$OS [M+H]+ (m/z): 233.3035, found: 233.3015.

Synthesis of Compound IIIe

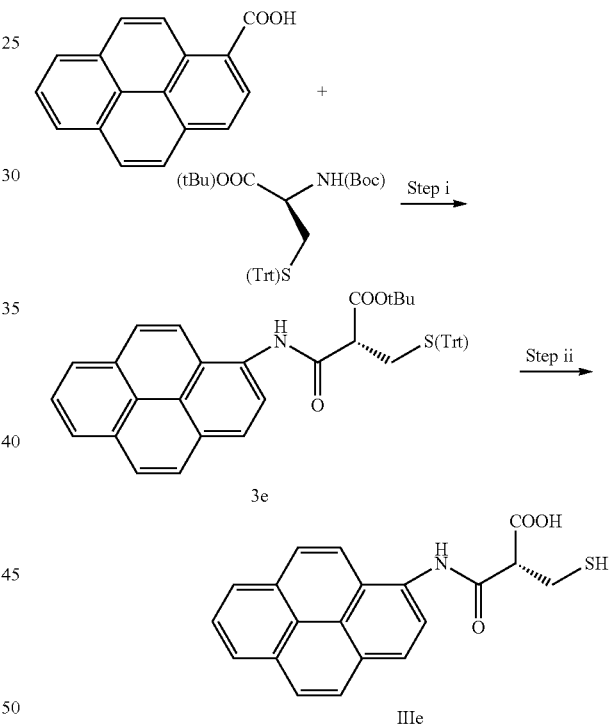

(R)-tert-butyl 2-(8,10-dihydropyrene-1-carboxamido)-3-(tritylthio)propanoate (3e). To a solution of pyrene carboxylic acid (250 mg, 1.06 mmol) in dry DMF (6 mL) EDC·HCl (681 mg, 3.55 mmol), HOBt (562 mg, 4.16 mmol) and DIPEA (1.25 mL, 9.13 mmol) were added. The reaction mixture was stirred during 2 min and H-Cys(Trt)-OtBu (468 mg, 1.12 mmol) was then added. The solution was stirred at room temperature under an inert atmosphere of Ar for 48 hours, and the formation of the product was followed by TLC. The mixture was diluted with DCM, washed with saturated aqueous NaHCO3 and saturated aqueous NaCl, and concentrated by distillation under reduced pressure. The crude product was purified by flash chromatography using EtOAc/Hexane as eluent (from 10% to 30% EtOAc to give 470 mg (77% yield) of 5e as a yellow solid.

$^1$H NMR (400 MHz, CDCl-d$_6$) δ=8.72 (d, 1H, CONH̲C*H), 8.32-8.08 (m, 8H, CH$_{Ar}$), 7.47 (dd, 6H, CH$_{Ar}$), 7.32-7.15 (m, 9H, CH$_{Ar}$), 6.64 (d, 1H, CH$_{Ar}$), 4.98 (dt, 1H, C*H̲), 2.96-2.81 13.04 (s, 1H, OH), 8.99 (d, 1H, CONH), 8.60 (d, 1H, CH$_4$), (m, 2H, C*HCH̲$_2$), 1.58 (s, 9H, CH$_3$) ppm. HRMS (ESL) calcd. for C43H37NO3S [M+H]$^+$ (m/z): 647.8330, found: 647.8310.

(R)-2-(8,10-dihydropyrene-1-carboxamido)-3-mercapto-propanoic acid (IIIe). To a solution of 5e (215 mg, 0.33 mmol) in DCM (1.5 mL), 1 mL of trifluoroacetic acid (TFA), 1,2-Ethanedithiol (EDT, 0.5 mL, 5.97 mmol) and triisobutylsilane (TIS, 1.30 mL, 4.98 mmol) were added rapidly and under stirring. The reaction mixture was stirred at room temperature for 2 hours, after which the solvents were partially evaporated using a N$_2$ flow. Diethyl ether was added over the reaction mixture and the product was filtered off and washed with diethyl ether. The product was purified by reversed-phase flash chromatography using a mixture of MeCN+0.07% (v/v) TFA and H2O+0.1% (v/v) TFA as mobile phase (gradient: from 0% to 10% MeCN in H2O). After lyophilisation 67 mg (58% yield) of 3e were obtained as a white solid.

$^1$H NMR (400 MHz, DMSO-d$_6$) δ=13.04 (s, 1H, OH̲), 8.99 (d1H, CONH̲), 8.60 (d, 1H, CH$_{Ar}$), 8.36 (dd. 3H, CH$_{Ar}$), 8.30-8.22 (m, 3H, CH$_{Ar}$), 8.16 (d, 1H, CH$_{Ar}$), 8.13 (t, 1H, CH$_{Ar}$), 4.71 (td, 1H, C*H̲), 3.14-2.89 (m, 2H̲$_2$SH). 2.70 (s, 1SH̲) ppm. HRMS (ESI$^+$) calcd. for C$_{20}$H$_{15}$NO$_3$S [M+H]$^+$ (m/z): 350.0851, found: 350.0839.

2. General Procedure for the Preparation of DCL Sensors and Fluorescence Analysis of the DCLs a) General Procedure for the Preparation of the DCL Sensors:

A 66.7 mM BIS-TRIS methane buffer was prepared by dissolving 1.39 g of the free amine in 100 mL of milli-Q water and adjusting the pH of the solution to 6.5 by the addition of HCl (aq). Individual concentrated stock solutions for the different building blocks (BBs) were prepared in DMSO. Mixture stock solutions containing the necessary BBs for the generation of the libraries (I, II and III) were prepared from these individual solutions. The reaction mixtures were then prepared by dilution of the stock solutions ensuring no differences in concentration between the reaction mixtures of the same batch.

Unless otherwise specified, the DCL sensors were prepared in the reaction mixtures at final concentrations of 0.1 mM for the bi- and tripodal BBs (I and II) and 0.05 mM of monopodal BB III, in a final 50 mM BIS-TRIS methane aqueous buffer (pH 6.5) with 25% DMSO.

The samples were prepared by adding 15 µL of the stock mixture in DMSO to 45 µL of the 66.7 mM buffered solution, to a final volume of 60 µL.

According to this general procedure, the following dynamic library sensors composed of a mixture of compounds were prepared:

Ia, IIa, IIIa
Ia, IIa, IIIb
Ia, IIa, IIIc
Ia, IIa, IIId
Ia, IIa, IIIe b) General Procedure for the Fluorescence Analysis of the DCLs:

Once the oxidation of the free thiols was complete (measured by HPLC or L-MS) the reaction mixtures were analyzed by fluorescence spectroscopy.

For the DCLs performed at 0.05 mM of III, the fluorescence samples were prepared by diluting the reaction mixture to a final volume of 2060 µL with a solution of 50% 100 mM BIS-TRIS aqueous buffer and 50% DMSO, reaching a final theoretical concentration of 1.5 µM for III. The mixtures containing a different concentration of III were diluted to reach a final concentration of 1.5 µM. Therefore, for measurement purposes the samples were diluted 1:34 with H$_2$O/DMSO (1:1 (v:v)) prior to the data acquisition. After studying the effect of the DMSO in the sensing system it was found that using a buffered solution at 50 mM with 50% DMSO to perform the measurements was optimal to avoid precipitation/aggregation processes and bleaching of the excimer signal.

After determining the different fluorescence spectra of all the DCLs, DCL formed by compounds Ia, IIa and IIIa was selected for further studies.

3. Evaluation of the Sensivity and Selectivity of the Method of the Invention

The compound IIIa presents suitable fluorescence spectra of its reduced and oxidized ([IIIa]$_2$) forms. Thus, [IIIa]$_2$ presents an excimer emission band at about 500 nm that is not present in the monomer, which is characterized by a low-wavelength band with fine structure (c.a. 350-450 nm). A library containing Ia and IIa (0.1 mM each), and IIIa (0.05 mM) minimizes the formation of [IIIa]$_2$ homodimer as read by LC-MS and fluorescence spectroscopy, with almost no excimer emission (FIG. 1, dotted line). When cysteine (IVa) is added to the reaction media the excimer band increases (FIG. 1, grey lines to black) due to the formation of [IIIa]$_2$.

The emission at 501 nm is detected after adding a Cys concentration as low as 50 µM and increasing the concentration of Cys (IVa) results in an increase of the fluorescent response (FIG. 2). This can be ratiometrically read by analyzing the excimer (501 nm) over monomer (385 nm) emission relationship. Thus, taking into account this ratio, the response to the presence of Cys goes from 1.4 (50 µM) to 3.8 (1 mM) times the blank. Considering that the normal presence of Cys in urine is ~35 µM and the occurrence of stone-producing cystinuria starts from approximately 0.8 mM, thus this method fits within these values.

Figure 2A:
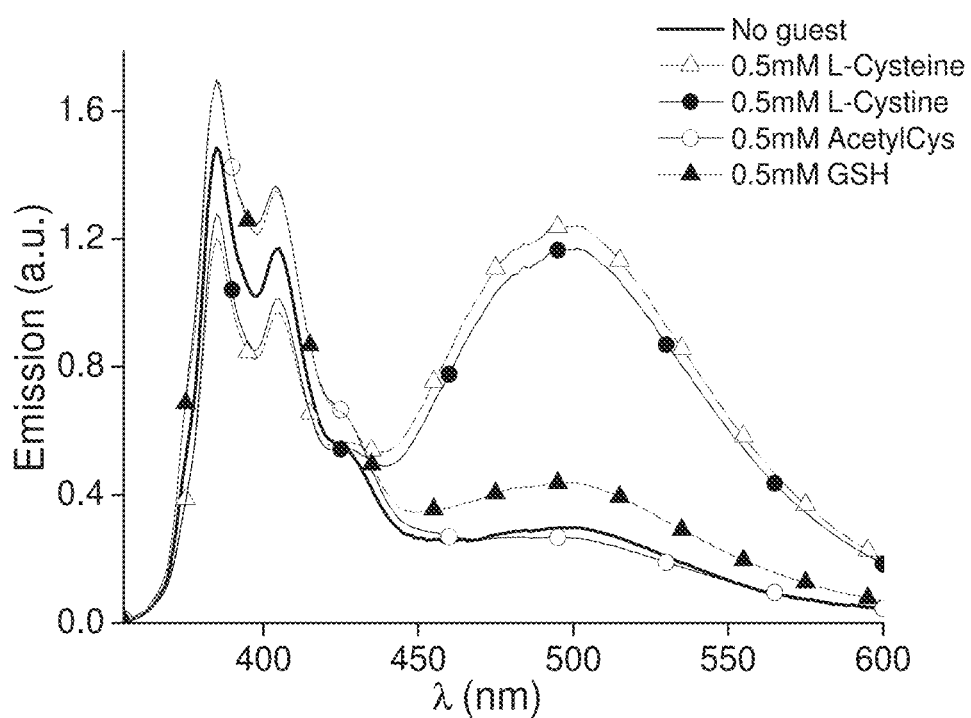
FIG. 2A: shows the fluorescence emission spectra of the library formed by Ia, IIa and IIIa alone (black line) and in the presence of 0.5 mM Cys (Δ), 0.25 mM cystine (●), 0.5 mM N-acetyl-Cys (○) and 0.5 mM GSH (▲).

Thanks to the dynamic nature of the sensing system based on disulfide formation and exchange, presence of Cystine (CySS or IVb) behaves similar to Cys (FIG. 2A, ● and Δ, respectively).

This ability, allows this dynamic sensor detecting cysteine in its reduced or oxidized forms in aqueous media with no need for an extra preparation step.

Selectivity

Selectivity in Front of Other Thiols such as GSH or N-acetylcysteine

The system of the invention, preferably that formed by Ia, IIa and IIIa, gives almost no response to the presence of other biologically relevant cysteine derivatives like GSH (FIG. 2A, ▲) or N-acetylcysteine (FIG. 2A, ○), overcoming the possible incidence of false-positives.

Figure 2B:
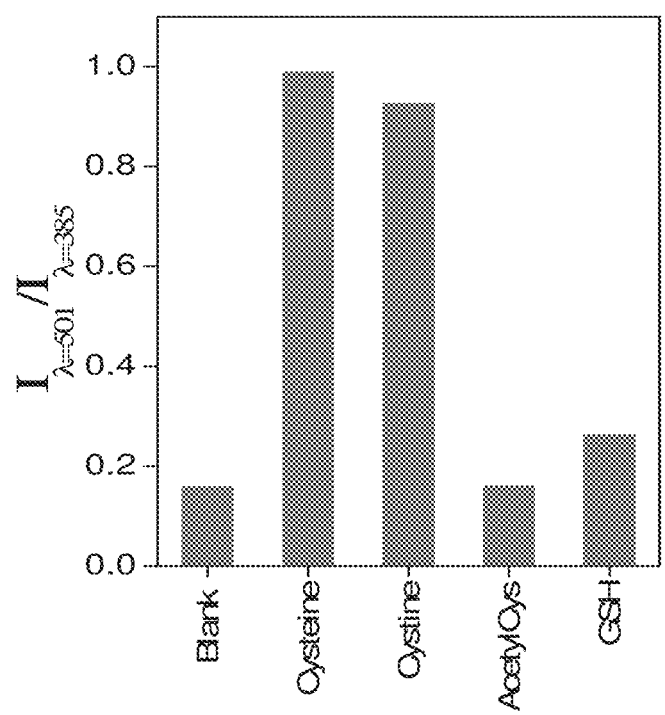
FIG. 2B shows the plot of the excimer/monomer ratio for the different biothiols.
Figure 2C:
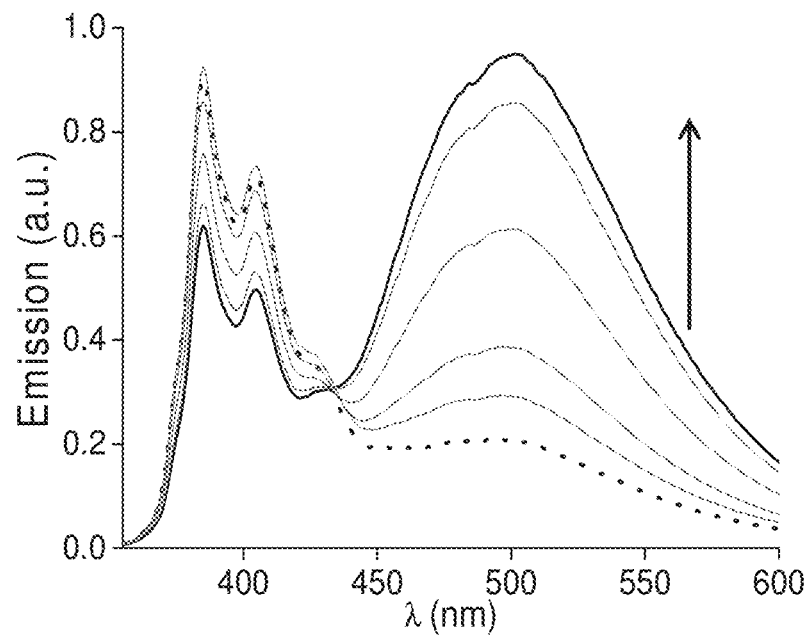
FIG. 2C and FIG. 2D show the sensing of Cys (0-1.0 mM) and CySS (0-0.5 mM)) respectively, in the presence of the three basic amino acids (Lys, Orn and Arg) at non-pathological upper limit concentrations found in urine.
Figure 2D:
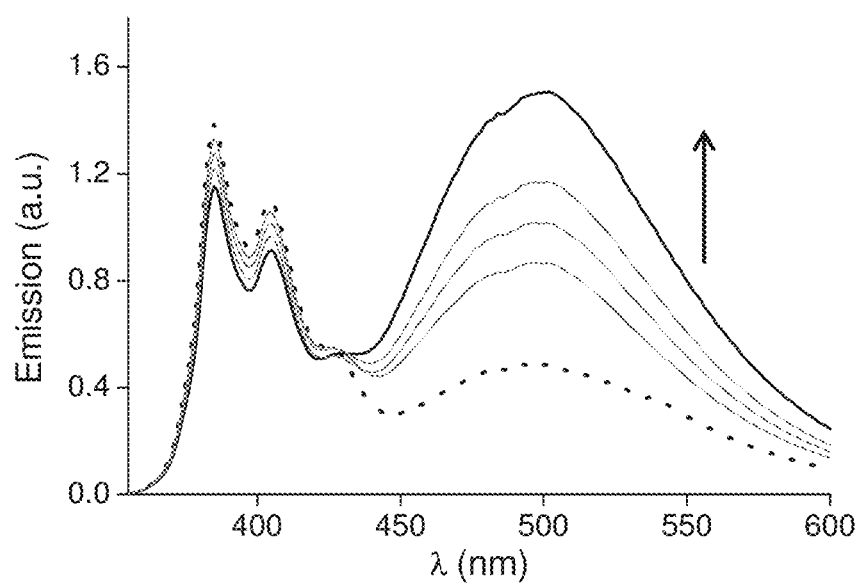

The selectivity for IVa and IVb is illustrated in FIG. 2B by the excimer/monomer ratio plot.

Cross Reactivity

Additionally, the behavior of the dynamic sensor system in the presence of the amino acids that can be typically found in urine was also tested, either at normal or pathological concentrations.

Figure 2E:
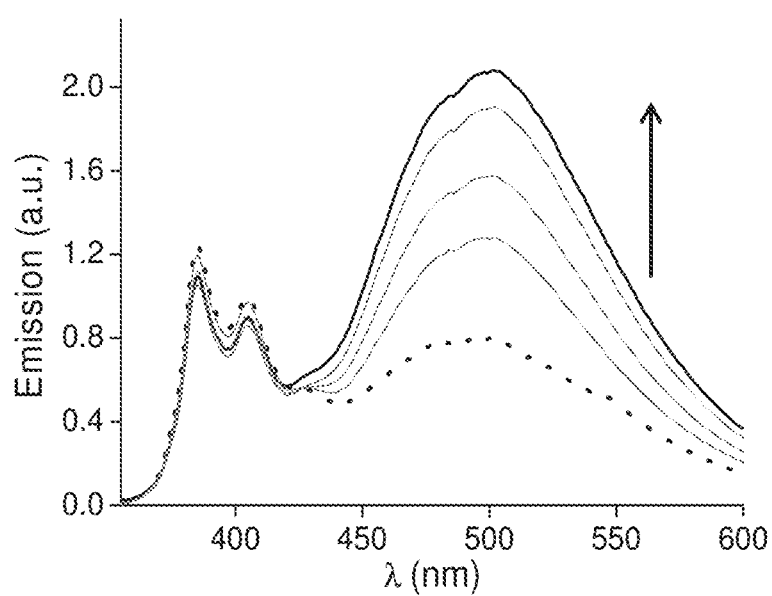
FIG. 2E and FIG. 2F show, as in FIG. 2C and FIG. 2D, but at pathological concentrations in urine samples (5 mM Lys, 1.4 mM Orn and 1.2 mM Arg). [Cys] or [CySS]=No L-Cys (dotted line), 0.05 mM, 0.1 mM, 0.25 mM, 0.5 mM.
Figure 2F:
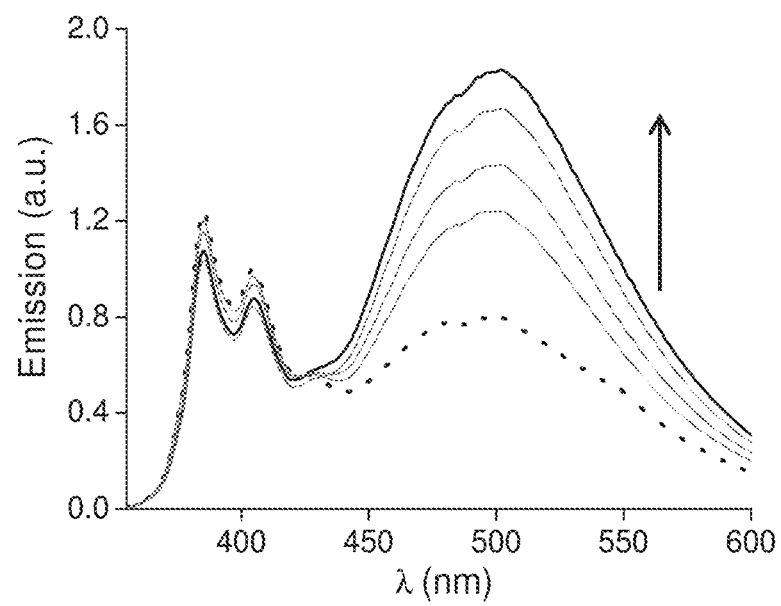

It was started with the basic amino acids (Lys, Orn, Arg), because they also show high values in cystinuria patients. The dynamic sensor (Ia, IIa and IIIa) is able to detect IVa and IVb (FIG. 2C and FIG. 2D) in the presence of these basic amino acids at concentrations in the upper limit of the expected in regular urine samples. More importantly, the sensor also provides a clear readout of IVa (Cys) in the presence of pathological concentrations of these basic amino acids (FIG. 2E and FIG. 2F).

This highlights the robustness of the network sensor, which is able to detect the much lower concentrations of the thiol analytes in the presence of potentially competing high concentrations of basic amino acids.

Figure 2G:
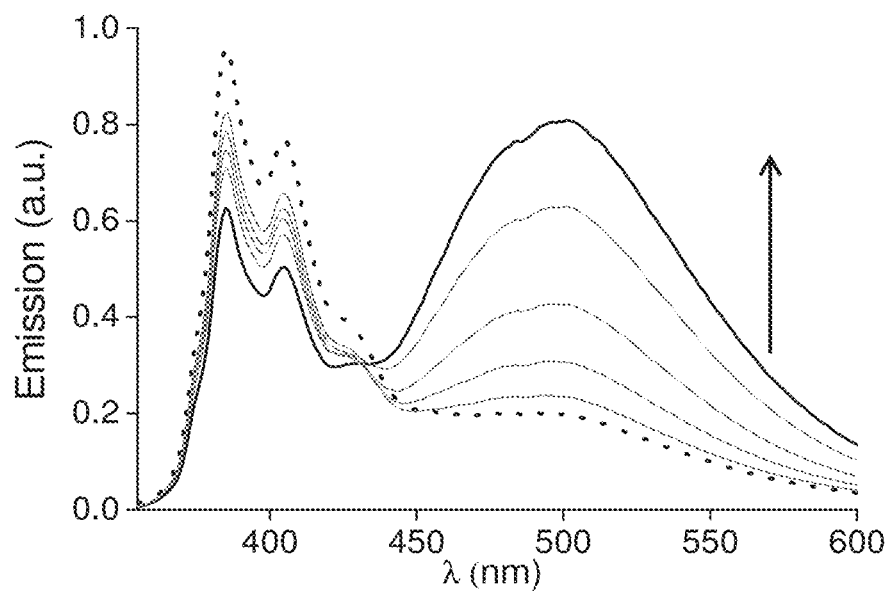
FIG. 2G shows, as in FIG. 2C but in a buffer containing (Lys, Orn, Arg, Asn, Gly, Ala, His, Asp, β-Ala, Ser, Tyr and Met). [Cys]=No L-Cys (dotted line), 0.05 mM, 0.1 mM, 0.25 mM, 0.5 mM, 1 mM.

Likewise, the sensor responded very efficiently to minute concentrations of both Cys and cystine in an extremely competitive media containing most of the amino acids that can be found in urine (Lys, Orn, Arg, Asn, Gly, Ala, His, Asp, β-Ala, Ser, Tyr, Met) at their physiological concentrations (FIG. 2G).

4. Measuring of Cystine Levels in Urine Samples

Once evaluated the sensitivity and the selectivity of the method, the dynamic sensing system was tested in real samples with urine from healthy volunteers.

General Procedure for the Preparation of the DCLs in Human Urine:

300 mM BIS-TRIS methane buffer was prepared as explained above.

Individual stocks of the building blocks (BBs) Ia, IIa and IIIa in DMSO were prepared. The DCLs were prepared in the reaction mixtures at final concentrations of 0.1 mM for Ia and IIa and 0.05 mM of IIIa in a final 50 mM BIS-TRIS methane aqueous buffer urine solution (pH 6.5) with 25% DMSO.

The samples were prepared by adding 15 μL of the stock mixture to 45 μL of the 300 mM buffered urine solution (containing 35 μL of urine sample and 10 μL of 300 mM buffered solution), to a final volume of 60 μL. The system was spiked with different concentrations of Cys (IVa).

General Procedure for the Fluorescence Analysis of the DCLs:

Once the oxidation of the free thiols was complete, each reaction mixture was analyzed by fluorescence spectroscopy.

The fluorescence samples were prepared by diluting the reaction mixture to a final volume of 2060 μL with a solution of 50% 100 mM BIS-TRIS aqueous buffer and 50% DMSO, reaching a final theorical concentration of 1.5 μM for IIIa. Therefore, for measurement purposes the samples were diluted 1:34 with 1:1 $H_2O$/DMSO (v:v) prior to the data acquisition.

Eleven samples of different volunteers were tested, and three extra measures of the combination of two samples for avoiding cross response were tested too (Table 1). The fluorescence spectra of the urine without added sensor were measured to confirm that no other metabolites in this fluid could interfere with the analysis. The positive response of the sensor to the naturally excreted cysteine was also measured.

TABLE 1

Selected real samples of urine from healthy volunteers used for test the sensing system described.

| Sample's Number | Volunteer Age | Gender |
|---|---|---|
| 1 | 29 | F |
| 2 | 24 | F |
| 3 | 34 | F |
| 4 | 38 | F |
| 5 | 29 | F |
| 6 | 30 | M |
| 7 | 23 | M |
| 8 | 62 | F |
| 9 | 65 | M |
| 10 | 34 | F |
| 11 | 27 | F |
| 12 (1 + 6) | 29 + 30 | F + M |
| 13 (2 + 7) | 24 + 23 | F + M |
| 14 (8 + 9) | 62 + 65 | F + M |

Figure 3A:
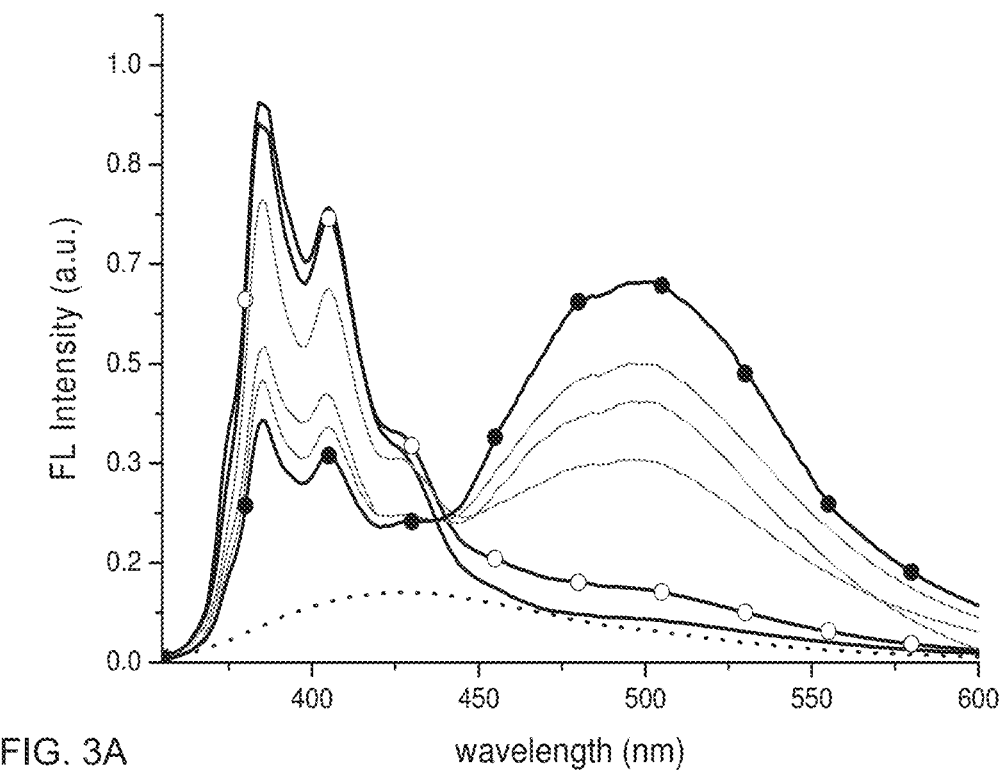
FIG. 3A: Shows the selected normalized fluorescence spectra of urine (dotted line), sensor alone (solid black line), sensor+urine (○) and after increasing concentrations of added Cys (0.25, 0.5, 1 mM (grey) to 2.5 mM (●)).
Figure 3B:
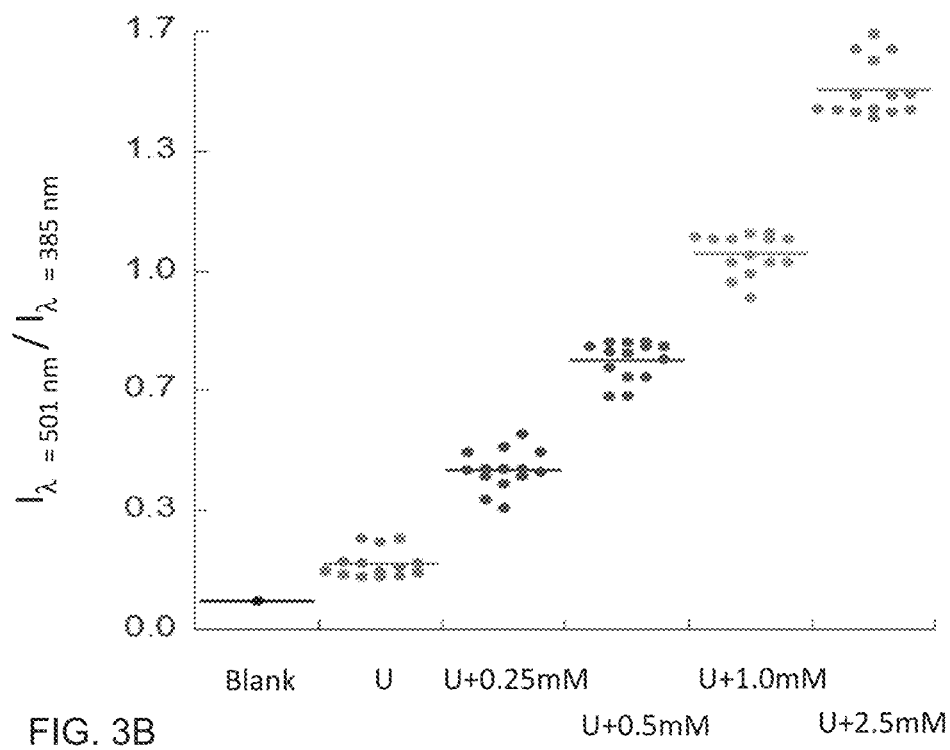
FIG. 3B shows the scatter plot of the excimer/monomer emission of the library alone (Blank), for different urine (U) samples of healthy volunteers and for the urine samples plus additional Cys.

The fluorescence spectra of the urine without added sensor was carried out to confirm that no other metabolites in this fluid could interfere with the analysis (FIG. 3A, dotted line). The positive response of the sensor to the naturally excreted cysteine in the urine samples was also measured (solid black line with empty circles in FIG. 3A and U samples in FIG. 3B). Moreover, the addition of cysteine (IVa) into the sample produced the increase of the band at 501 nm, with a detection range that goes from normally occurring Cys in urine (U in FIG. 3B) to pathological concentrations (U+1.0, 2.5 mM, grey). Thus, we could also sense abnormal concentrations of cysteine that would not yet cause calculi (U+0.25, 0.5 mM, black).

The invention claimed is:

1. A mixture of molecules comprising at least a compound as defined by formula (I):

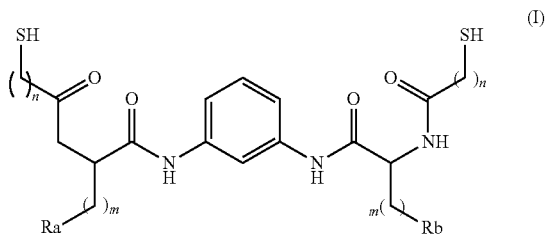

or an isomer or a salt thereof, wherein:

Ra and Rb are independently selected from H, —CONRR', —COOR, —NRR', —OH, —C(NH)$NH_2$, —CH(OH)$CH_3$, aryl-($C_6$-$C_{10}$) or heteroaryl-($C_6$-$C_{10}$);

R and R' are independently selected from H or alkyl-($C_1$-$C_5$);

m is an integer selected from 0, 1, 2, 3 or 4;

n is an integer selected from 1 or 2;

at least a compound of formula (II):

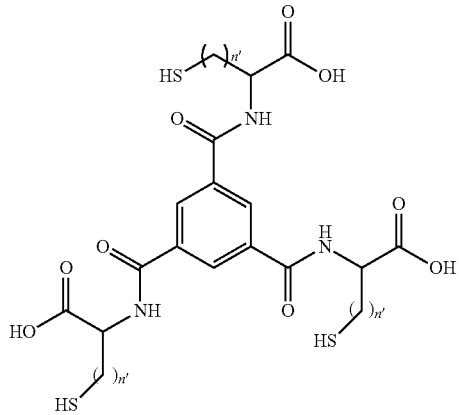

(II)

or an isomer or a salt thereof, wherein:
n' is an integer selected from 1 or 2;
and at least a compound of formula (III):

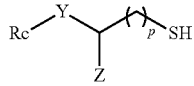

(III)

or an isomer or a salt thereof, wherein:
Rc represents an aromatic chromophore;
Y is selected from NHCO or CONH;
Z is selected from H, —$NH_2$, —OH or —COOH;
p is an integer selected from 0, 1, 2 or 3.

2. The mixture of molecules according to claim 1, which also comprises at least a compound of formula (IV):

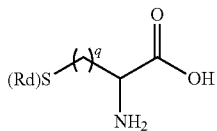

(IV)

or an isomer or a salt thereof, wherein:
Rd is selected from H or S($CH_2$)qCH($NH_2$)COOH;
q is an integer selected from 1, 2 or 3.

3. The mixture of molecules according to claim 1, wherein m is 1 and n is 1.

4. The mixture of molecules according to claim 1, wherein Ra is $CONH_2$.

5. The mixture of molecules according to claim 1, wherein Rb is $CONH_2$.

6. The mixture of molecules according to claim 1, wherein n' is 1.

7. The mixture of molecules according to claim 1, wherein Rc is selected from the following chromophores:

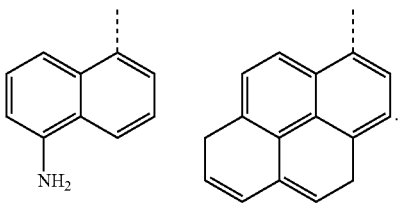

8. The mixture of molecules according to claim 1, wherein Y is —NHCO.

9. The mixture of molecules according to claim 1, wherein Z is —$NH_2$.

10. The mixture of molecules according to claim 1, wherein p is 1.

11. The mixture of molecules according to claim 1, wherein Rd is H.

12. The mixture of molecules according to claim 1, wherein q is 1.

13. A dynamic combinatorial library comprising the mixture of molecules claim 1.

14. An in vitro method for the detection of a compound of formula (IV):

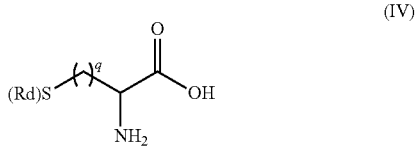

(IV)

or an isomer or a salt thereof, wherein:
Rd is selected from H or S($CH_2$)qCH($NH_2$)COOH;
q is an integer selected from 1, 2 or 3
in a sample comprising the following steps:
a) mixing at least a compound of formula (I) with at least a compound of formula (II) and at least a compound of formula (III) according to claim 1;
b) contacting the sample comprising the compound of formula (IV) with the mixture of step (a);
c) measuring the fluorescence emission of the mixture obtained in step (b);
d) detecting a significant deviation from a standard; and
e) assigning the sample to the group of samples comprising a compound of formula (IV) when a significant difference has been detected in stage (d).

15. The method according to claim 14, wherein the molecule of formula (IV) is selected from cysteine or cystine.

16. A kit for the detection of a compound of formula (IV) in a sample of

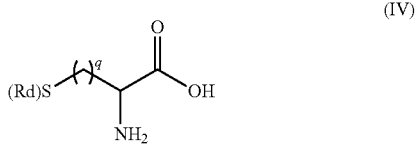

(IV)

or an isomer or a salt thereof, wherein:
Rd is selected from H or S($CH_2$)qCH($NH_2$)COOH;
q is an integer selected from 1, 2 or 3, comprising a mixture of compounds of formula (I), (II) and (III) as described in claim 1.

* * * * *

UNITED STATES PATENT AND TRADEMARK OFFICE
CERTIFICATE OF CORRECTION

PATENT NO. : 11,905,236 B2
APPLICATION NO. : 17/042667
DATED : February 20, 2024
INVENTOR(S) : Ignacio Alfonso Rodriguez, Jordi Sola Oller and Maria Lanfuente Fabra It is certified that error appears in the above-identified patent and that said Letters Patent is hereby corrected as shown below:

In the Claims

Column 24, Claim 1, Line 50, the formula appears to be missing the inclusion of NH, please amend the formula to appear as follows -- 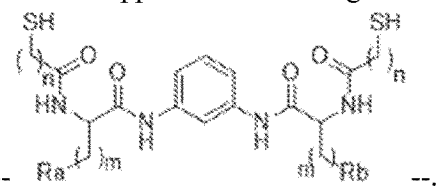 --.

Column 26, Claim 13, Line 23, after "molecules" insert --of--.

Signed and Sealed this
Fourteenth Day of January, 2025

Derrick Brent
*Acting Director of the United States Patent and Trademark Office*